United States Patent [19]
Harpel

[11] Patent Number: 4,849,353
[45] Date of Patent: * Jul. 18, 1989

[54] IMMUNOCAPTURE OF ENZYME INHIBITOR, ENZYME COMPLEXES AND USES THEREOF

[75] Inventor: Peter C. Harpel, New York, N.Y.

[73] Assignee: Cornell Research Foundation, Inc., Ithaca, N.Y.

[*] Notice: The portion of the term of this patent subsequent to Dec. 16, 2003 has been disclaimed.

[21] Appl. No.: 712,473

[22] Filed: Mar. 15, 1985

Related U.S. Application Data

[63] Continuation of Ser. No. 287,665, Jul. 28, 1981, abandoned, which is a continuation-in-part of Ser. No. 192,166, Sep. 30, 1980, abandoned.

[51] Int. Cl.$^4$ ............... G01N 33/564; G01N 33/573; C12Q 1/00; C12Q 1/56; C12N 9/99
[52] U.S. Cl. ................................. 435/7; 435/4; 435/13; 435/23; 435/184; 435/810; 436/506
[58] Field of Search ............... 435/4, 7, 23, 24, 188, 435/13, 17, 810, 184; 436/501, 507, 518, 807, 506

[56] References Cited

U.S. PATENT DOCUMENTS

| | | | |
|---|---|---|---|
| 3,730,435 | 5/1973 | McKie | 435/23 |
| 3,834,990 | 9/1974 | Werle et al. | 435/197 |
| 3,886,136 | 5/1975 | Claeson et al. | 260/112.5 |
| 3,932,221 | 1/1976 | Pfleiderer | 435/24 |
| 4,020,268 | 4/1977 | Nishikawa et al. | 536/1 |
| 4,046,634 | 9/1977 | Mercer | 435/815 |
| 4,066,505 | 1/1978 | Schneider | 260/112 R |
| 4,100,028 | 7/1978 | Stepanov et al. | 435/815 |
| 4,134,792 | 1/1979 | Boguslaski et al. | 435/188 |
| 4,198,335 | 4/1980 | Collen | 23/230 B |
| 4,231,999 | 11/1980 | Carlsson et al. | 435/7 |
| 4,233,401 | 11/1980 | Yoshida et al. | 435/810 X |
| 4,273,866 | 6/1981 | Voss et al. | 435/184 |
| 4,332,783 | 6/1982 | Pernice et al. | 435/7 |
| 4,342,566 | 8/1982 | Theofilopoulos et al. | 23/230 B |
| 4,353,982 | 10/1982 | Gomez et al. | 435/7 |
| 4,629,694 | 12/1986 | Harpel | 435/13 |

FOREIGN PATENT DOCUMENTS

| | | |
|---|---|---|
| 0032204 | 12/1980 | European Pat. Off. . |
| 0038935 | 3/1981 | European Pat. Off. . |
| 2952478 | 7/1981 | Fed. Rep. of Germany . |
| 3016575 | 11/1981 | Fed. Rep. of Germany . |

OTHER PUBLICATIONS

Monji et al, "Steric Hinderance Enzyme Immunoassay (SHEIA)", Res., *Comm. Chem. Path. Pharm.*, vol. 26, No. 1 (1979), pp. 187–196.

(List continued on next page.)

*Primary Examiner*—Esther M. Kepplinger
*Attorney, Agent, or Firm*—Jones, Tullar & Cooper

[57] ABSTRACT

This invention relates to methods for detecting, identifying and quantifying enzymes, for example, human proteolytic enzymes. The method broadly comprises forming an immobilized or insoluble complex comprising enzyme, enzyme inhibitor and enzyme inhibitor-antibody reactive site and then detecting and identifying, preferably quantitatively, one or more enzymes bound to the complex, or one or more inhibitor antibodies bound to the complex to indirectly detect one or more bound enzyme.

In a preferred embodiment, a matrix, e.g. solid or semisolid surface or permeable matrix, has affixed thereto enzyme inhibitor-antibody or an immonologically active (inhibitor binding) fragment of such an antibody. This insoluble enzyme inhibitor interacting matrix is then contacted with biological fluid, e.g. body fluid, to bind one or more predetermined enzyme inhibitor-enzyme complexes, if present in the biological fluid. The bound enzyme is then detected, identified and preferably quantified.

In another preferred embodiment, a matrix has affixed thereto an antibody against the enzyme sought which is capable of binding one or more predetermined enzymes present in biological fluid as an enzyme inhibitor complex. The bound enzyme, enzyme inhibitor complex is then characterized by detecting and preferably quantifying the bound enzyme inhibitor, thus indirectly identifying and preferably quantifying the bound enzyme or enzymes.

13 Claims, 6 Drawing Sheets

OTHER PUBLICATIONS

Harpel, et al., "Degradation of Human Fibrinogen by Plasma $\alpha_2$-Macroglobulin-Enzyme Complexes", *J. Clin. Invest.*, vol. 52 (1973), pp. 2175–2184.

Plow et al, "Immunochemical Characterization of the Plasmin-Antiplasmin System, Basis for the Specific Detection of the Plasmin-Antiplasmin Complex by Latex Agglutination Assays". *J. Lab. Clin. Med.*, vol. 93, No. 1 (1979), pp. 197–209.

Lau, et al., "The Isolation and Characterization of a Specific Antibody Population Directed Against the Prothrombin Activation Fragments $F_2$ and $F_{1_{2}}$", *J. Biol. Chem.*, vol. 254, No. 18 (1979), pp. 8751–8761.

Ohlsson et al., "Demonstration and Semiquantitative Determination of Complexes Between Various Proteases and Human $\alpha_2$-Macroglobulin", *Clin. Chim. Acta*, vol. 66 (1976), pp. 1–7.

Harpel, et al, "Heat-Induced Fragmentation of Human $\alpha_2$-Macroglobulin", *J. Bio. Chem.*, vol. 254, No. 17, pp. 8669–8678 (1979).

"The Chemistry and Physiology of Human Plasma Proteins" (Bing Ed.), Pergamon Press 1979, pp. 385–399.

"Methods in Enzymology, Proteolytic Enzymes" (L. Lorand Ed.), Academic Press (1976), pp. 639–651.

"Progress in Hemostasis and Thrombosis", vol. III (Spaet Ed.), Grune & Stratton (1976), pp. 145–189.

Harpel et al., *Analytical Biochem.*, 108:166–175 (1980).

Harpel, *J. Clin. Invest.*, 68:46–55 (1981).

Lewin et al, *J. Biological Chem.*, 258:6415–6421 (1983).

Brower et al, *Blood*, 61:842–849 (1983).

Inman et al, *Clin. Exp. Immunol.*, 53:521–528 (1983).

Jesty et al, *Analytical Biochem.*, 139:158–167 (1984).

Levin et al, *J. Clin. Invest.*, 74:571–580 (1984).

IMMUNOCAPTURE OF ENZYME INHIBITOR, ENZYME COMPLEXES AND USES THEREOF

The invention described herein was at least in part made in the course of work under a grant or award from the Department of Health, Education and Welfare (Grant No. HL 18828, Department of Health & Human Services).

CROSS-REFERENCE TO RELATED APPLICATION

This application is a continuation of application Ser. No. 287,665, filed July 28, 1981, now abandoned, which in turn is a continuation-in-part of application Ser. No. 192,166, filed Sept. 30, 1980 now abandoned.

BACKGROUND OF THE INVENTION

Many processes in the biological systems, e.g. animals and humans are mediated by the activation of proteinases. Some of these processes are constructive processes such as the blood clotting system; others are destructive, such as the food digesting enzymes in the gastrointestinal tract. Indirect evidence suggests that inappropriate or uncontrolled activation of proteolytic enzymes such as that which occurs in thrombosis or disseminated intravascular coagulation or other inflammatory conditions leads to tissue injury and human disease. The ability to identify and quantitate active proteinases in the blood and other body fluids has been limited by the fact that these enzymes when activated in blood or released by cells into fluids become complexed with various naturally occuring inhibitors.

At least eight distinct blood proteins have been characterized as inhibitors of protein cleaving enzymes. These inhibitors are also found in a variety of body fluids. The most important of these inhibitors appear to be alpha 2-plasmin inhibitor, alpha 2-macroglobulin, alpha 1-anti-trypsin, C1 inhibitor and antithrombin-heparin cofactor. These inhibitors have a broad specificity in that each of these inhibitor proteins can form a complex with a variety of proteolytic enzymes. The ability to measure these enzyme-inhibitor complexes in fluids would aid in the diagnosis and therapy of diseases involving enzyme activation. Methods to identify and to quantitate the enzyme in complex with its inhibitor have not been satisfactorily developed.

Approaches utilized by other investigators involve the production of an antibody directed against antigens in the enzyme inhibitor complex that are not shared by either one of the constituents alone. These antibodies have been produced against the alpha 2-plasmin inhibitor, plasmin complex by Plow et al. [*J. Lab Clin. Med.*, 93:199–209 (1979)]; and against the antithrombin, thrombin complex by several investigators [Lau et al., *J. Biol. Chem.*, 254:8751–8761 (1980)]. The former technique employs the detection of the plasmin-antiplasmin complex by latex agglutination assay, and the latter by a radioimmunoassay. These methods are promising, however, the development of an antibody in animals directed against new antigens within the enzyme-inhibitor complex has proven to be difficult.

As pointed out hereinafter alpha 2-macroglobulin ($\alpha_2$M), proteinase complexes are a particularly useful group of complexes within the scope of this invention. The majority of proteinases complexed to $\alpha_2$M loose most of their reactivity with detecting antibodies. Thus an immunologic detecting system would not permit quantitation cf the bound enzyme.

The $\alpha_2$M is a plasma protein with a wide spectrum of proteinase inhibiting activity [Harpel et al, *Progress in Hemostasis and Thrombosis*, T. H. Spaet, Ed., Grune & Stratton, Inc., New York, (1976) 3: 145–189]. It has been shown by a variety of investigators, as reviewed by Harpel, supra, and Starkey et al., *Proteinases in Mannalian Cells and Tissues*, A. J. Barrett, ed., Elsevier, Amsterdam, (1977) pp. 663–696, that $\alpha_2$M binds with a remarkably varied group of protein cleaving enzymes derived from blood, circulating white blood cells, tissues, invading bacteria, plants and snake venoms. Schultz et al., *Z. Naturforsch*, 10b(8):463–473 (1966), isolated $\alpha_2$M from human scrum and Wallenius et al., *J. Biol. Chem.*, 225:253–267 (1957), distinguished $\alpha_2$M from IgM, the other serum globulin with a 19S sedimentation constant. Haverback et al., *J. Clin. Invest.*, 41:972–980 (1962), first demonstrated the $\alpha_2$M bound trypsin or chymotrypsin, and observed that the hydrolytic activity of the complexed enzyme was retained against low molecular weight substrates but almost totally inhibited against large substrates such as proteins; [see also Harpel et al., *J. Clin. Invest.*, 52:2175–2184 (1973)]. The ability of $\alpha_2$M to bind proteinases without completely inhibiting the active enzymatic site of its bound enzyme is distinctive as compared to other blood proteinase inhibitors that completely inactivate the active site of the proteinases.

The identification of $\alpha_2$M-proteinase complexes in biologic fluids has been accomplished by Ohlssen et al., *Clin. Chim. Acta*, 66:1–7 (1976), by his observation that the $\alpha_2$M enzyme complex has a different isoelectric point than does the free incomplexed $\alpha_2$M. Other investigators, including the inventor, have isolated $\alpha_2$M from blood by chromatographic techniques and have measured the activity of the putative $\alpha_2$M enzyme complex using small molecular weight proteinase substrates. Inherited deficiency of $\alpha_2$ plasmin inhibitor is associated with a life-long hemorrhagic diathesis characterized by rapid dissolution of fibrin thrombi. Lijnen et al., *J. Biol. Chem.*, 255:10214–10222 (1980) and Aoki et al., *Blood*, 55:483–488 (1980). In purified systems, comparing the distribution of plasmin between $\alpha_2$-macroglobulin, C1 inactivator and $\alpha_2$-antitrypsin, the $\alpha_2$-macroblobulin binds the majority of the enzyme; Harpel, *Fed. Proc.*, 34:344 (1974) (Abstract). In studies from our laboratory examining the binding of plasmin in mixtures of purified $\alpha_2$-plasmin inhibitor and $\alpha_2$-macroglobulin, the plasmin inhibitor bound over 90 percent of the added plasmin; Harpel, *J. Exp. Med.*, 146:1033–1040 (1977). These and other studies suggest that $\alpha_2$-plasmin inhibitor is the physiologically most important inhibitor of plasmin mediated fibrinolysis; Aoki et al., *J. Clin. Invest.*, 60:361–369 (1977) and Aoki et al., *Thrombos. Haemostas.*, 39:22–31 (1978).

BRIEF DESCRIPTION OF THE DRAWINGS

FIG. 4 is a graphic representation of the binding of plasma $\alpha_2$M-$^{125}$I-trypsin complexes by solid-phase $\alpha_2$M antibody. Varying concentrations of $^{131}$I-trypsin (as indicated on the abscissa) were added to a mixture of $^{125}$I-$\alpha_2$M and plasma (diluted ¼). Following a 10 min incubation, 0.2 ml portions were mixed for 2 hours with solid-phase $\alpha_2$M antibody (50 μl packed gel). The pellets were harvested by centrifugation, washed 4 times with 1.0 ml PBS, and counted for $^{125}$I and $^{131}$I in a dual channel gamma counter. The gels were then assayed for amidolytic activity utilizing the substrate BzPhe-Val-Arg-NHNp as indicated in the Example. The activity is corrected for the spontaneous activity associated with the plasma to which no trypsin was added. The points are fitted by linear regression analysis.

FIG. 6 A model of the enzyme linked differential antibody immunosorbent assay for plasmin inhibitor-plasmin complexes. PI=either $\alpha_2$-plasmin inhibitor or $\alpha_2$-macroglobulin; RaPI=rabbit anti-inhibitor IgG fraction; Ra Plasmin=rabbit anti-plasminogen F(ab')$_2$ fraction; E=alkaline phosphatase; pNPP=p-nitrophenyl phosphate.

FIG. 7 Plasminogen standard curve. Human plasminogen, diluted from 1.25 to 25 ng/ml in carbonate buffer was applied to the plastic wells for 18 hours, 4° C. After washing, the enzyme labeled immonospecific rabbit F(ab')$_2$ anti-plasminogen was added. Following an 18 hour incubation and washing, the substrate p-nitrophenyl phosphate was added and color development followed in a Titertek Multiscan photometer.

FIG. 8 Generation of $\alpha_2$-plasmin inhibitor-plasmin, $\alpha_2$-macroglobulin-plasmin complexes by the addition of plasmin to plasma as measured by the enzyme-linked differential antibody immunosorbent assay. Increasing concentrations of plasmin (0.5 to 2.4 μg/ml plasma) were added to plasma. Following incubation for 10 min at 37° C., the plasma was diluted 40 fold with PBS-Tween buffer containing 0.05 EACA, and samples were added to microtitration plates coated with rabbit anti-$\alpha_2$-plasmin inhibitor, anti-$\alpha_2$-macroglobulin or normal rabbit IgG, and assayed as detailed in the Methods. The results are expressed as plasminogen equivalents by converting the readings to fmol plasminogen/ml utilizing a standard plasminogen curve (see FIG. 2). The curves are fitted by linear regression analysis. For the $\alpha_2$-plasmin inhibitor-plasmin complex curve (first 5 data points), $y=0.547x+7.89$; and for the $\alpha_2$-macroglobulin-plasmin complex curve, $y=0.043x-3.15$.

FIG. 9 Generation of $\alpha_2$-plasmin inhibitor-plasmin, $\alpha_2$-macroglobulin-plasmin complexes by the addition of urokinase to plasma as measured by the enzyme-linked differential antibody immunosorbent assay. Increasing concentrations of urokinase (31.25 to 500 units/ml plasma) were added to plasma and incubated 30 min at 37° C. The plasma was diluted forty-fold in PBS-Tween-EACA buffer and assayed for $\alpha_2$-plasmin inhibitor-plasmin and $\alpha_2$-macroglobulin-plasmin complexes as described in Methods. For $\alpha_2$-plasmin inhibitor-plasmin complex curve (first 5 data points), $y=0.285x+2.85$; and for $\alpha_2$-macroglobulin-plasmin complex curve, $y=0.091x-2.55$.

FIG. 10 Quantitation of purified $\alpha_2$-plasmin inhibitor-plasmin, and $\alpha_2$-macroglobulin-plasmin complexes by enzyme-linked differential antibody immunosorbent assay. Varying concentrations of plasmin (0.128 to 2.048 μg) were added to either $\alpha_2$-plasmin inhibitor (6.0 μg) or $\alpha_2$-macroglobulin (200 μg) and the volume adjusted to 4.0 ml with PBS-Tween buffer containing 0.05 M EACA. The concentration of inhibitor used represents a 1/40 dilution of that amount found in normal plasma. Samples were applied to microtitration plates coated with either rabbit anti-$\alpha_2$-plasmin inhibitor or anti-$\alpha_2$-macroglobulin IgG and processed as detailed in Methods. The plasmin concentration added to the inhibitor was converted to nmol/l following multiplication by 40. For the $\alpha_2$-plasmin inhibitor-plasmin complex curve (first 5 data points), $y=0.475x+7.9$; and for the $\alpha_2$-macroglobulin-plasmin complex curve, $y=0.242x+3.2$.

FIG. 11 Percent $\alpha_2$-macroglobulin-plasmin complex generated in plasmin or urokinase-treated plasma as assessed by the enzyme-linked differential antibody immunosorbent assay. The relative amount of plasmin bound to $\alpha_2$-macroglobulin or to $\alpha_2$-plasmin inhibitor in plasmin or urokinase-treated plasma in FIGS. 3 and 4, was calculated from the purified inhibitor-plasmin curves of FIG. 5. The percent activity of the $\alpha_2$- macroglobulin-plasmin complex in either the plasmin or urokinase-plasma compared to the total activity of both complexes is plotted against the activity of the $\alpha_2$-plasmin inhibitor-plasmin complex in each treated plasma.

DESCRIPTION OF THE INVENTION

This invention relates to methods for detecting, identifying and quantifying enzymes, for example, proteolytic enzymes. One method broadly comprises forming an insoluble complex (E-I-anti I) comprising enzyme (E), enzyme inhibitor (I), and then detecting and identifying and preferably quantitating one or more enzymes bound to the complex. In a preferred embodiment, a matrix (M), e.g. solid or semisolid surface or permeable matrix has affixed thereto an enzyme inhibitor-antibody or enzyme inhibitor-antibody immunologically active (inhibitor-binding) fragment of such an antibody (anti I). This insoluble matrix is then contacted with biological fluid, e.g. body fluid, to bind one or more predetermined or suspected enzyme inhibitor-enzyme complexes (I-E) in the biological fluid. The bound enzyme is then detected, identified and preferably quantified.

Another method broadly comprises forming an insoluble complex comprising antibody for the enzymes sought to be measured or an enzyme reacting fragment of such an antibody, which antibody or fragment is capable of binding one or more predetermined enzymes present in biological fluid as an enzyme inhibitor complex through the enzyme present in the complex in essentially the same manner it would bind the free enzyme. The bound enzyme, enzyme inhibitor complex is then reacted with adapted antibody for the enzyme inhibitor contained in the bound enzyme, enzyme inhibitor complex, which enzyme inhibitor antibody has been adapted to be measured, for example, with a detectable label. The bound enzyme, enzyme inhibitor complex is then characterized by detecting and preferably quantifying the bound enzyme inhibitor antibody, thus indirectly identifying and preferably quantifying the bound enzyme or enzymes.

Enzyme inhibitor (I) as defined for the purpose of this invention and useful in this invention includes not only materials which complex with the enzyme in a biological system, but also includes inhibitors such as $\alpha_2 M$ which form enzyme complexes wherein the enzymatic activity of the enzyme is restricted, but not completely prevented. This latter type of inhibitor is the inhibitor measured in the second above disclosed method. For example, $\alpha_2 M$-proteinase complexes have been shown to retain hydrolytic activity against low molecular weight substrates, but are almost totally enzymatically non-reactive to large substrates such as proteins.

Methods suitable for detecting and quantifying the bound enzyme are generally known. Generally, after the immobilized E-I-anti I complex has been removed from contact with the biological fluid, the bound enzyme can be reacted in one of two general methods. The first method comprises a reaction with a detection facilitating material which reacts with a site specific to the bound enzyme or enzymes or the bound E-I complex sought and which either has a detectable group or atom measurable by an analytical technique such as a radioactive tag atom, an I.R. or U.V. light absorbing group, or which causes a visible color change; or which generates a a detectable cleavage product, a leaving compound or ion, which in turn is measurable by an analytical technique. This class of reaction is not dependent on the enzymatic action of the enzyme which may be biologically inactive in the E-I complex. The second method comprises an enzymatic reaction of the bound enzyme in cases such as $\alpha_2 M$ where the bound enzyme retains activity against selected substrates. In such a case the immobilized E-I-anti I complex is contacted with a substrate reactive with the bound enzyme, which substrate upon reaction, by color change or the generation of a readily measurable system-unique cleavage product susceptable to analytic detection, allows analytical determination.

Methods suitable for detecting and quantifying the bound inhibitor antibody in the second general method are also generally known. Generally after an immobilized enzyme antibody-E, I complex has been removed from contact with the biological fluid, the bound inhibitor in the bound E, I complex is reacted with antibody for said inhibitor which inhibitor antibody has been adapted by modification with a detectable group or atom measurable by an analytical technique such as a radioactive tag atom, an I.R. or U.V. light absorbing group or any other measurable phenomenon such as generally described above.

In some instances in the preparation of an anti I, as in the case in the Example where the IgG fraction of rabbit antihuman $\alpha_2 M$ antiserum displayed activity toward an enzyme detecting substrate, it may be necessary to react, as in the example or to further purify, as through the use of chromatographic technique, the anti I to prevent interference with subsequent analysis. Alternatively, at least in come instances, this spurious activity can be measured and compensated for in the analytical determination.

It is further noted that many inhibitors are capable of binding more than one particular enzyme. Since the immobilized E-I-anti I complexes are stable, it is possible to employ seriatum several techniques which are capable of distinguishing between individual bound enzymes in the immobilized E-I-anti I complex. This is especially true where the detection mechanism generates a measurable leaving product rather than binding or blocking reactive sites. Again this is especially applicable to the second of the above described detecting reactions, since the substrates chosen seriatum may be substrates which have reactivity to only one or more specific group of enzymes potentially present in the enzymatically active E-I-anti I complex.

Given the process of the invention, quantitating the analytical results is generally within the skill of the art. At least one such method comprises quantitating I bound to the E-I-anti I complex so that final quantitation can be expressed as a function of bound inhibitor (I). This can be accomplished by adding a small amount of labeled inhibitor to the biological fluid. The amount of label in the E-I-anti I complex is then measured. This is proportional to the binding of native inhibitor.

Preferably the identification and quantification of the enzyme complexed in the immobilized inhibitor, enzyme complex is carried out in one of two ways. Where the complex is enzymatically active, as $\alpha_2 M$, reaction with substrates is employed. For enzyme complexes which are not enzymatically active antibodies are prepared against the specific enzyme of interest. Thus, for example, antibodies may be prepared in rabbits or goats against the human blood proteinases plasmin, thrombin, kallikrein, Cl (the first component of complement), factor Xa, Hageman factor; or against human pancreatic enzymes trypsin, elastase or chymotrypsin; against human polymorphonuclear leukocyte (white blood cell) neutral proteinases such as elastase, collagenase and cathepsin G; or against proteinase released from damaged tissues such as cathepsin B. Such antibodies have been produced in a number of laboratories.

If desired, the immunoglobulin fraction of the antisera or the specific antibody molecules, isolated for example by affinity chromatography, are then labeled with alkaline phosphatase or other detecting enzyme by methods detailed by Engvall et al., *Immunochemistry*, 8:871 (1971) and others, or alternatively by use of a radioactive tagging material such as $NaI^{125}$.

The insoluble immunocaptured enzyme, inhibitor complex is then incubated with a specific antienzyme antibody such as above, and after a suitable time the unbound antibody is removed by washing. The anti-enzyme antibody remains bound to the enzyme in the immobilized inhibitor complex. The anti-enzyme antibody is then measured for example by determining the activity of the alkaline phosphatase or radioactivity linked to the detecting anti-enzyme antibody. The amount of enzyme bound is quantitated, for example, using standardized curves consisting of purified inhibitor, enzyme complexes. The use of a detecting antibody per se is a known technique which functions well in the context of the immunocapture technique of the invention.

It is pointed out that the biological fluids being surveyed are dynamic systems in which the enzyme balance or content may change due to influences present after the state sought to be measured. For example, if the study of enzymes in a human blood sample is undertaken, it is noted the clotting grossly changes the enzymatic or E-I complex content of the blood. Thus, care must be taken in that case to prevent clotting. Likewise, to the extent possible, all enzyme or E-I complex altering factors should be avoided by the appropriate selection of reactants and equipment materials. Alternatively, where possible the extraneous enzymatic changes caused during handling and processing can be accounted for and the analytical results appropriately considered or corrected.

One immobilized or insoluble complex of the invention comprises (E-I-anti I), i.e. enzyme, enzyme inhibitor and inhibitor antibody or active fragment thereof. In the preferred embodiment the complex is affixed to a solid or semi-solid matrix. The only essential requirement is that the ultimate E-I-anti I complex be immobilized. This may first result only upon the ultimate combination of E or E-I complex with the anti I to form, for example, a precipitate. But preferably an immobilized matrix-anti I entity is preformed and then contacted with biological fluid containing E-I complex. Another possible mode is the addition of anti-I to E-I complex containing biological fluid with the subsequent immobilization, e.g. affixation to a matrix, of the preformed mobile E-I-anti I entity.

The second method of the invention, starting with immobilized enzyme antibody, can be conducted in a similar manner with the steps modified to the appropriate materials.

The precise nature of the matrix in either method of the invention is not critical beyond the fact that there can be affixed thereto anti I on the one hand and anti E on the other hand in a manner such that the anti I or anti E moiety can be affixed thereto by some means, for example, chemical e.g. covalent bonding or absorption, adsorptions, or the like, in a manner so that the anti I remains reactive with E-I complex. The matrix may be solid or permeable and may be in particulate form, for example, or may comprise, for example, for at least a portion of the structure of a container or be in a unit removable associated with a container.

The biological fluid surveyed can be virtually any human, animal, microbiological, or vegetable fluid containing enzymes or E-I complexes. Body fluids such as blood, urine, or pleural, joint and peritoneal fluids can be analyzed by this technique.

EXAMPLE I

This example demonstrates that purified $\alpha_2 M$ as well as $\alpha_2 M$-trypsin complexes are quantitatively bound to rabbit anti-human $\alpha_2 M$ antibody that is immobilized on a gel matrix. This example further demonstrates that the antibody bound $\alpha_2 M$-trypsin complexes possess amidolytic activity that can be readily assayed while attached to the particulate gel. The enzymatic activity of these insolubilized $\alpha_2 M$-trypsin complexes is identical to that of fluid phase $\alpha_2 M$-enzyme complexes. These techniques, utilizing purified systems, have been extended to human plasma to which radiolabeled trypsin and a trace amount of radiolabeled $\alpha_2 M$ are added. Using the insoluble antibody technique of the invention, $\alpha_2 M$-trypsin complexes are quantitatively recovered from plasma as measured both by bound radioactivity and by the capacity of the antibody-bound complex to hydrolyze a synthetic tripeptide chromogenic substrate.

Purification of $\alpha_2$-Macroglobulin -$\alpha_2$-macroglobulin was isolated from fresh human plasma in the presence of soybean trypsin inhibitor as previously described; Harpel, *Methods* Enzymol; 45:639–652 (1976). $\alpha_2 M$ was labeled with $^{125}I$ by the method of McFarlane; McFarlane, *Biochem. J. (London);* 62:135–143 (1956). 0.5 mCi of carrier-free sodium $^{125}I$ iodide was added to 1.7 mg $\alpha_2 M$ in 1.0 ml borate buffer (0.2M) pH 8.0, containing NaCl(0.16M). Iodine monochloride (0.05 ml containing 0.007 micromoles ICl) was added with mixing. After a 10-min incubation at room temperature, the unbound iodide was removed by Sephadex G-25 (Pharmacia) gel filtration chromatography. The specific activity of the radiolabeled $\alpha_2 M$ was 0.2 $\mu Ci/g$.

Purification of $\beta$-trypsin - $\beta$-trypsin was prepared from crystallized, dialyzed salt-free lyophilized bovine trypsin (Worthington) as described by Yung and Trowbridge; *Biochem. Biophys. Res. Commun.*, 65:927–930 (1975). The specific activity of the final product was 95% as determined by active site titration with p-nitrophenyl-p'-quanidinobenzoate HCL; Chase et al, *Methods Enzymol.,* 19:20–27 (1970). This preparation, following reduction, consisted of a single protein band as identified by dodecyl-sulfate gel (9%-acrylamide) electrophoresis [Weber et al, *Methods Enzymol.,* 26:3–27 (1972)] indicating that the single chain $\beta$-form had been isolated from the original mixture of $\alpha$-4 and $\beta$-trypsin and inactive material. The tyrpsin was stored at $-70°$ C. in HCL (1 mM) containing $CaCl_2$ (10 mM) and NaCl (0.1 M). $\beta$-trypsin was labeled with $^{131}I$ by the method of McFarlane, supra. $\beta$-trypsin was dialyzed against borate buffer (0.2 M), pH 8.0 containing benzamidine (0.01 M, Aldrich Chemical Co.), and NaCl (0.16 M). 0.5 mCi of carrier-free $^{131}I$-sodium iodide was added to 1.5 mg $\beta$-trypsin in a total volume of 1.0 ml borate-benzamidine buffer. Iodine monochloride (0.05 ml containing 0.2 micromole ICl) was added with mixing. After a 10-min incubation at room temperature the free iodide and benzamidine were removed by gel filtration chromatography. The labeled preparation was dialyzed against HCl (1 mM) containing NaCl (0.1 M) prior to storage at $-70°$ C. The specific activity of the radiolabeled $\beta$-trypsin was 0.2 $\mu Ci/\mu g$.

Preparation of rabbit antihuman $\alpha_2 M$ antisera - New Zealand white rabbits were immunized by intradermal injection of $\alpha_2 M$ mixed with Freund's adjuvant. The antisera produced one immunoprecipitation arc on double diffusion analysis against human plasma and demonstrated a reaction of identity with the starting antigen.

The IgG fraction of the antisera was prepared by chromatography on DEAE-cellulose. This IgG fraction was found to hydrolyze N-benzoyl-L-phenylalanyl-L-valyl-L-arinine-p-nitroanilide HCl (BzPhe-Val-Arg-NHNp; S-2160), however the activity was inhibited by treatment of the IgG material with α-N-p-tosyl-L-lysine chloromethyl ketone HCl (TLCK) (0.01 M) for 3 days at 4° C. followed by extensive dialysis. The TLCK treated IgG was coupled to Bio-Gel A-5m (Bio-Rad Laboratores) by the cyanogen-bromide method as detailed by March et al, *Anal. Biochem.*, 60:149-152 (1974). Coupling to the activated gel was carried out in citrate buffer (0.2 M), pH 6.5, using 6.0 mg IgG per ml activated gel. Coupling efficiency was greater than 90%. After the coupling procedure, the gel was incubated 1 h in 1.0 M enthanolamine pH 8.0 to neutralize any remaining protein binding groups. The IgG fractions of normal rabbit serum, and rabbit antisera directed against human albumin or human haptoglobin were also prepared and coupled to Bio-Gel A-5m as detailed above.

Studies of the binding of $\alpha_2 M$ to immobilized rabbit antihuman $\alpha_2 M$ antibody. The gel containing the bound $\alpha_2 M$ antibody was diluted twofold (V/V) with phosphate buffer (0.05M), pH 7.2, containing NaCl (0.2M) (PBS). This coupled antibody was incubated with $^{125}I$-$\alpha_2 M$, $^{125}I$-$\alpha_2 M$-$\beta$-trypsin complexes, or with plasma containing a trace quantity of $^{125}I$-$\alpha_2 M$ and varying concentrations of $^{131}I$-$\beta$-trypsin as indicated in the figure legends. All incubations were at room temperature, in volumes of 1.0 ml or less, with constant mixing by end over end inversion using a Labquake® mixer (Labindustries, Berkeley, CA). The incubation was terminated bl centrifugation and the pelleted insoluble $\alpha_2 M$ antibody gel washed repeatedly with 1.0 ml portions of PBS. The pellets were counted for associated $^{125}I$ or $^{131}I$ radioactivity in a Searle 1185 dual channel $\gamma$ counter.

Assay of the amidolytic activity of $\alpha_2 M$-$\beta$-trypsin complexes in the fluid phase or bound to immobilized $\alpha_2 M$ antibody. Soluble trypsin or $\alpha_2 M$-trypsin complexes were assayed by methods similar to those previously detailed; Svendsen et al, *Thromb. Res.*, 1:267-278 (1972). The substrate N-benzoyl-L-phenylalanyl-L-valyl-L-arginine-p-nitroanilide hydrochloride (BzPhe-Val-Arg-NHNp=S-2160, obtained from Ortho Diagnostics, Inc.; or from Vega Biochemicals) was dissolved in distilled water (0.7 mg/ml). $\beta$-trypsin, or $\alpha_2 M$ trypsin complexes were made to a volume of 0.4 ml with Tris-HCL (0.1 M), pH 8.3, containing CaCl$_2$ (1.25 mM). Substrate (0.2 ml) was added and the mixtures were incubated at room temperature. The reaction was terminated at varying intervals by the addition of 30% acetic acid (0.2 ml) followed by the addition of 0.6 ml of the Tris-CaCl$_2$ buffer to achieve a final volume of 1.4 ml. The absorbance at 405 nm was measured with a Gilford 240 spectrophotometer. The concentration of p-nitroanalide released was determined using a molar absorbancy of 10,500; Aurell et al, *Thromb. Res.*, 11:595-609 (1977).

To determine the amidolytic activity of $\alpha_2 M$-trypsin complexes bound to gel-coupled rabbit anti-human $\alpha_2 M$ IgG, Tris-CaCl$_2$ buffer (0.4 ml) and BzPhe-Val-Arg-NHNp (0.2 ml) were added to the immobilized antibody gels that had been incubated with $\alpha_2 M$-trypsin complexes. After incubation for varying time periods at room temperature, the antibody containing gel was removed by centrifugation. 30% acetic acid (0.2 ml) was added to the supernatant, followed by the addition of 0.6 ml Tris-CaCl$_2$ buffer. The absorbance at 405 nm was measured, and the results expressed (following correction for the substrate blanc) either as $\mu$ moles p-nitroanilide released/liter/min, or when the amount of $\alpha_2 M$ bound was determined, as $\mu$ moles/liter/min/mg $\alpha_2 M$.

For the derivation of Michaelis-Menton constants, $\beta$-trypsin (0.25 $\mu$g/ml), $\alpha_2 M$ (50 $\mu$g/ml), and a trace quantity of $^{125}I$-$\alpha_2 M$ were incubated at 0° C. in PBS. Assay of this incubation mixture for free $\beta$-trypsin, using the high molecular weight particulate substrate Ramazolbrilliant blue hide [Hayes et al, The Physiological Inhibitors of Blood Coagulation and Fibrinolysis, Collen et al, eds., Elsevier, Amsterdam, 1979, pp. 273-280], proved negative and indicated that all of the $\beta$-trypsin had been bound by the $\alpha_2 M$. Portions (0.2 ml) of the $\alpha_2 M$-$\beta$-trypsin incubation mixture were then incubated in duplicate with rabbit anti $\alpha_2 M$-IgG coupled to Bio-Gel A-5m (10 $\mu$l packed gel). The duplicate gel incubation mixtures were washed four times each with 1.0 ml PBS and the $^{125}I$, a measure of $\alpha_2 M$ bound to the gel, was determined. The insolubilized $\alpha_2 M$-$\beta$-trypsin complexes were then assayed in duplicate for the ability to hydrolyze varying concentrations of BzPhe-Val-Arg-NHNp. Due to the fact continuous kinetic measurements could not be made with the insolubilized $\alpha_2 M$-enzyme complexes, duplicate assays were terminated at discrete time intervals of 5, 10 and 15 minutes at each substrate concentration and the concentration of liberated p-nitroanilide determined.

Portions of the original soluble $\alpha_2 M$-$\beta$-trypsin mixtures, containing an amount of radioactivity equivalent to that bound to the antibody gels described above were assayed in duplicate at varying substrate concentrations. In this case, production of p-nitroanilide was followed continuously at 405 nm in a Gilford 240 recording spectrophotometer equipped with a Honeywell 1800 recorder. Km and Vmax for the soluble and immobilized $\alpha_2 M$-$\beta$-trypsin complexes were obtained from Lineweaver-Burk linear transformations of the initial reaction velocities and substrate concentrations.

Electroimmunoassay. The concentration of native $\alpha_2 M$ in plasma, or in plasma supernatants following incubation with immobilized $\alpha_2 M$ antibody was determined by the electroimmunoassay, rocket technique described by Laurell; *Scand. J. Clin. Lab. Invest.*, 29 (Suppl. 124):21-37 (1972)

Amidolytic activity of $\alpha_2 M$-trypsin complexes in the fluid phase or bound to immobilized rabbit anti-human $\alpha_2 M$ antibody. The hydrolytic activity of $\alpha_2 M$-trypsin complexes were assessed using the chromogenic substrate BzPhe-Val-Arg-NHNp. $\beta$-trypsin was incubated with a mixture of unlabeled and $^{125}I$-labeled $\alpha_2 M$ at trypsin:$\alpha_2 M$ molar ratios of 0.6, 0.3, and 0.15, well below the 2 moles of $\beta$-trypsin per mole $\alpha_2 M$ binding capacity of $\alpha_2 M$ established in a previous study. The amidolytic activity of these mixtures was found to be linear with time and proportional to the concentration of $\beta$-trypsin in the system. The $\beta$-trypsin-$\alpha_2 M$ mixtures were also incubated with the IgG fraction of rabbit anti-human $\alpha_2 M$ antiserum coupled to Bio-Gel A-5m. After extensive washing the gel pellets were counted in a $\gamma$ counter for $^{125}I$ and were found to have bound 88% of the $^{125}I$-$\alpha_2 M$ radioactivity of the original incubation mixture indicating that the majority of the $^{125}I$-$\alpha_2 M$ in the incubation mixture has been bound to the immobilized antibody. The solid-phase antibody in the absence of $\alpha_2$M-trypsin mixture did not hydrolyze BzPhe-Val-Arg-NHNp, but the solid-phase $\alpha_2$M antibody which was incubated with trypsin-$\alpha_2$M complexes had gained amidolytic activity that was proportional to the amount of trypsin in the original fluid-phase incubation mixture. Incubation of the solid phase antibody with $\beta$-trypsin in the absence of $\alpha_2$M did not confer amidolytic activity upon the gel nor did the immobilized IgG fraction derived from normal rabbit serum bind either $\alpha_2$M or $\alpha_2$M-trypsin complexes. Thus, the activity gained when immobilized anti-human $\alpha_2$M antibody was incubated with the $\alpha_2$M-trypsin mixtures was a reflection of the specific binding of the $\alpha_2$M-trypsin complexes.

Figure 1:
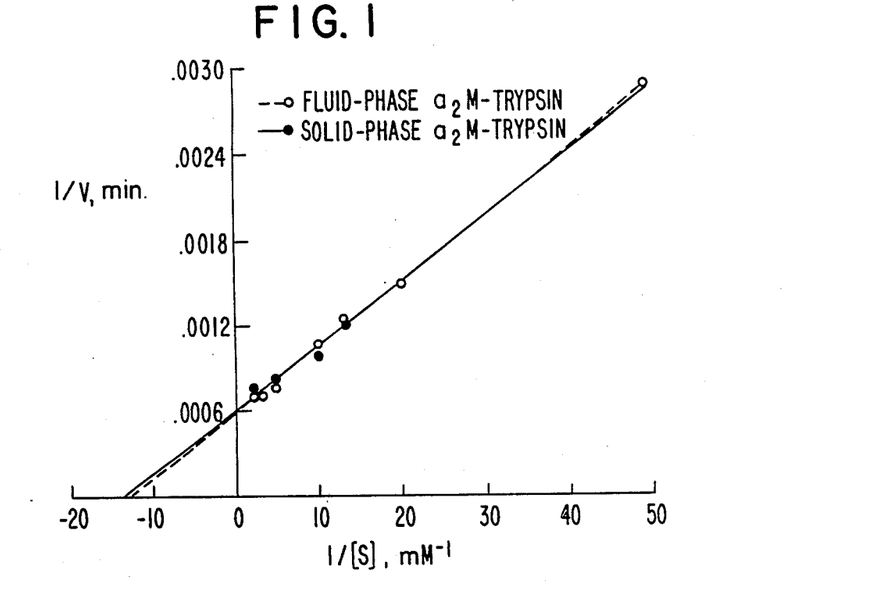
FIG. 1 is a Lineweaver-Burk plot of the hydrolysis of BzPhe-Val-Arg-NHNp by fluid-phase or by solid-phase antibody-bound $\alpha_2$M-$\beta$-trypsin complexes. The hydrolytic activity of $\alpha_2$M-$\beta$ trypsin complexes was determined as indicated in the Example. All determinations are in duplicate and the points are fitted by linear regression analysis.

Analysis of the kinetics of the hydrolysis of substrate in the fluid-phase by $\alpha_2$M-trypsin complexes as compared to the solid-phase complexes demonstrated no significant differences (FIG. 1). The Michaelis-Mention constants for the fluid-phase complexes as determined by LineweaverBurk plots were Km=0.079 mM and Vmax-1707 min$^{-1}$, and of the solid-phase $\alpha_2$M-trypsin complexes, Km=0.078 mM and Vmax=1700 min$^{-1}$. This indicates that under the experimental conditions detailed for these assays, the binding of the $\alpha_2$M-trypsin complex to a surface did not affect its amidolytic activity.

Effect of pH and ionic strength on the amidolytic activity of solid-phase antibody-bound $\alpha_2$M-trypsin complexes. Both soluble $\alpha_2$M-trypsin complexes and solid-phase antibody-bound $\alpha_2$M-trypsin complexes demonstrated a similar peak of amidolytic activity between pH 8.0 and 9.0. At higher pH's there was a significant decrease in substrate hydrolysis. In other experiments, the effect of variations in sodium chloride concentration (0 to 0.5 M) on the catalytic activity of the immobilized $\alpha_2$M-trypsin complex was studied. A broad unchanging peak of activity from 0.05 to 0.3 M NaCl was observed with a decrease in amidolytic activity at both 0 and 0.5 M NaCl. Both soluble and immobilized $\alpha_2$M-trypsin complexes behaved in a similar manner.

Effect of repetitive assays on the amidolytic activity of solid-phase antibody-bound $\alpha_2$M-trypsin complexes. In order to assess the stability of the immobilized antibody-bound $\alpha_2$M-trypsin complexes, four portions of the immobilized $\alpha_2$M antibody were incubated with an $\alpha_2$M-trypsin mixture containing a trace amount of $^{125}$I-$\alpha_2$M. After repeated washings, the gels were counted to determine the amount of bound $\alpha_2$M. The insolubilized antibody $\alpha_2$M-trypsin complex was then assayed for BzPhe-Val-Arg-NHNp hydrolytic activity. This procedure was repeated four times. As illustrated in Table I, the specific activity of the $\alpha_2$M-trypsin complex, bound to the immobilized antibody, did not change with repeated assays indicated that trypsin itself did not dissociate from the complex in the presence of the chromogenic substrate. There was a small equivalent loss of both $\alpha_2$M and amidolytic activity with repeated assays reflecting either loss of gel during the washings or elution of the $\alpha_2$M-trypsin complex.

TABLE 1

Effect of Repetitive Assays on the Amidolytic Activity of Insoluble Antibody-Bound $\alpha_2$ M-Trypsin Complexes[a]

| Assay No. | $\mu$g $\alpha_2$ M[b] | $\mu$moles/L/min[c] | Specific Activity ($\mu$moles/L/min/mg $\alpha_2$ M) |
|---|---|---|---|
| 1 | 6.7 ± 0.17 | 0.79 ± 0.03 | 117.9 ± 5.3 |
| 2 | 6.7 ± 0.16 | 0.76 ± 0.05 | 113.4 ± 5.4 |
| 3 | 6.5 ± 0.25 | 0.77 ± 0.04 | 118.5 ± 2.4 |
| 4 | 5.1 ± 0.65 | 0.60 ± 0.09 | 117.7 ± 6.3 |

[a]Portions (0.2 ml) of a mixture of $\alpha_2$M and $^{125}$I-$\alpha_2$M (50 $\mu$g/ml) and $\beta$-trypsin (300 ng) were incubated in quadruplicate for 2 hours with rabbit anti-human $\alpha_2$M-IgG coupled to Bio Gel A-5m (10 $\mu$l packed gel). Following washings of each sample four times with PBS, it was subsequently assayed for amidolytic activity by adding Tris-CaCl buffer, pH 8.3 (0.4 ml) and BzPhe-Val-Arg-NhNp (0.7 $\mu$g/ml), 0.2 ml) for 15 min at room temperature with mixing by inversion. After each assay, the samples were washed four times in succession and the amidolytic activity and radioactivity redetermined. This assay procedure was repeated a total of four times.
[b]The $\mu$g $\alpha_2$M bound to the beads was calculated as the counts bound/total counts x $\mu$g $\alpha_2$M in the original incubation mixture.
[c]All values in the table represent the mean of four determinations.

Figure 2:
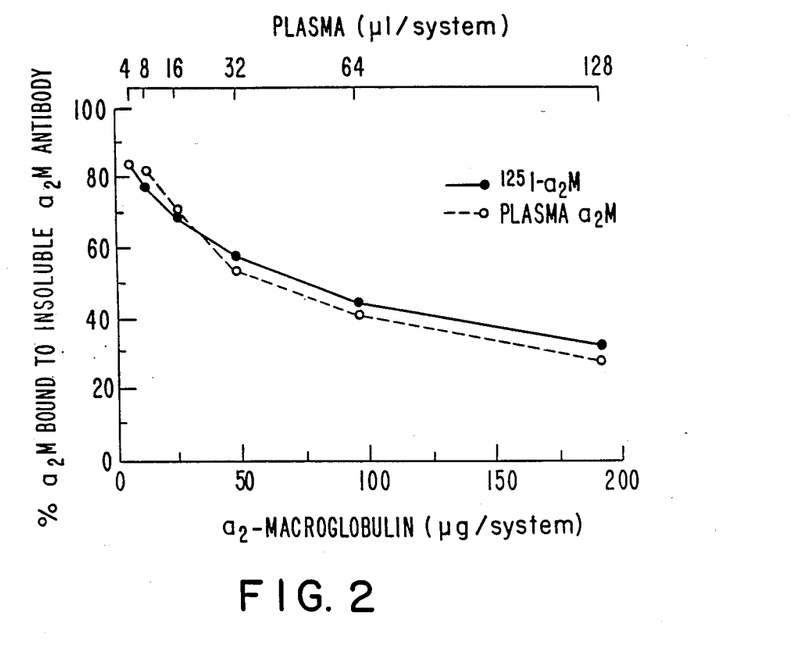
FIG. 2 is a graphic representation of the binding of $\alpha_2$M in plasma by solid-phase $\alpha_2$M antibody. Plasma containing 1.5 mg/ml $\alpha_2$M, as determined by electroimmunoassay, was diluted with PBS. A constant trace quantity of $^{125}$I-$\alpha_2$M was added to each dilution (0.1 μg). The amount of plasma added per incubation system is indicated at the top of the figure. Portions (0.2 ml) were incubated in duplicate for 2 hours with solid-phase $\alpha_2$M antibody (10 μl packed gel). Following separation of the gel by centrifugation the supernatant was assayed for $\alpha_2$M antigen concentration by electroimmunoassay, and the $^{125}$I-$\alpha_2$M bound to the beads measured. The unlabeled $\alpha_2$M from the plasma that was bound to the immobilized antibody was determined as that amount of $\alpha_2$M originally added to the antibody gel minus the remaining $\alpha_2$M in the supernatant as measured by electroimmunoassay. The counts bound are expressed as a percent of the total counts originally added to the immobilized antibody.

Studies on the binding of $\alpha_2$M in human plasma to immobilized anti-human $\alpha_2$M antibody. Experiments were designed to test whether the binding of purified $\alpha_2$M or $\alpha_2$M-trypsin complexes by solid-phase anti-human $\alpha_2$M antibody could be extended to a complex biological fluid such as plasma. In the study shown in FIG. 2, the solid-phase $\alpha_2$M antibody was incubated with serial dilutions of plasma to which $^{125}$I-$\alpha_2$M was added. The radioactivity bound to the insoluble antibody was measured. The native $\alpha_2$M in the starting plasma and the residual $\alpha_2$M in the plasma supernatant following absorption was also quantitated by electroimmunoassay. The results demonstrate that the binding of the $^{125}$I-$\alpha_2$M added to plasma by the immobilized antibody parallels the binding of native plasma $\alpha_2$M.

Specificity of binding of $^{125}$I-$\alpha_2$M added to plasma by the solid-phase $\alpha_2$M antibody was also tested by incubating plasma containing $^{125}$I-$\alpha_2$M with unmodified Bio-Gel A-5m, or this same gel to which the purified IgG fraction of normal rabbit serum, or the IgG fraction of rabbit antisera against either human albumin or haptoglobin was coupled. Under conditions in which greater than 95% of the radioactivity became bound to insoluble $\alpha_2$M antibody, less than 2% of the $^{125}$I-$\alpha_2$M radioactivity was associated with these other gel preparations.

Figure 3:
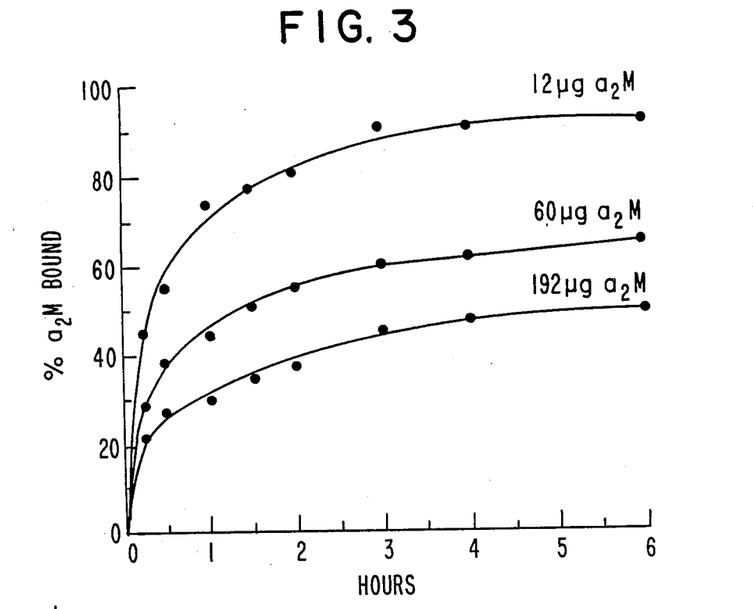
FIG. 3 is a graphic representation of the effect of time in incubation on the binding of $\alpha_2$M in plasma by solid-phase $\alpha_2$M antibody. Plasma containing 1.5 mg/ml $\alpha_2$M was diluted to 4, 20, and 64% with PBS containing a trace amount of $^{125}$I-$\alpha_2$M (0.1 μg/system). Portions (0.2 ml) were incubated in duplicate with immobilized $\alpha_2$M antibody (10 μl packed gel) and the reaction stopped by centrifugation at the intervals indicated on the abscissa. After washing four times in 1.0 ml PBS, the pellets were counted for $^{125}$I in a gamma counter and the counts bound expressed as a percent of the total counts originally added to the insoluble antibody. The amount of $\alpha_2$M contained in the plasma that was added to each incubation mixture is indicated.

The effect of time of incubation of plasma with solid-phase $\alpha_2$M antibody on the binding of $\alpha_2$M to the gel was investigated (FIG. 3). The antibody gel was incubated for varying time period with three different dilutions of plasma which contained 12, 60 and 192 $\mu$g $\alpha_2$M respectively. There was a progressive increase in binding throughout the six hour incubation period at all concentrations of $\alpha_2$M. At the lowest concentration of $\alpha_2$M (12 $\mu$g/system), 91.7% of the $\alpha_2$M was bound after 6 hours. At the highest concentration of $\alpha_2$M, 49% or 94 $\mu$g of $\alpha_2$M was bound. This indicates that 1.0 ml of the $\alpha_2$M antibody gel has the capacity to bind at least 9.4 mg $\alpha_2$M.

Figure 4:
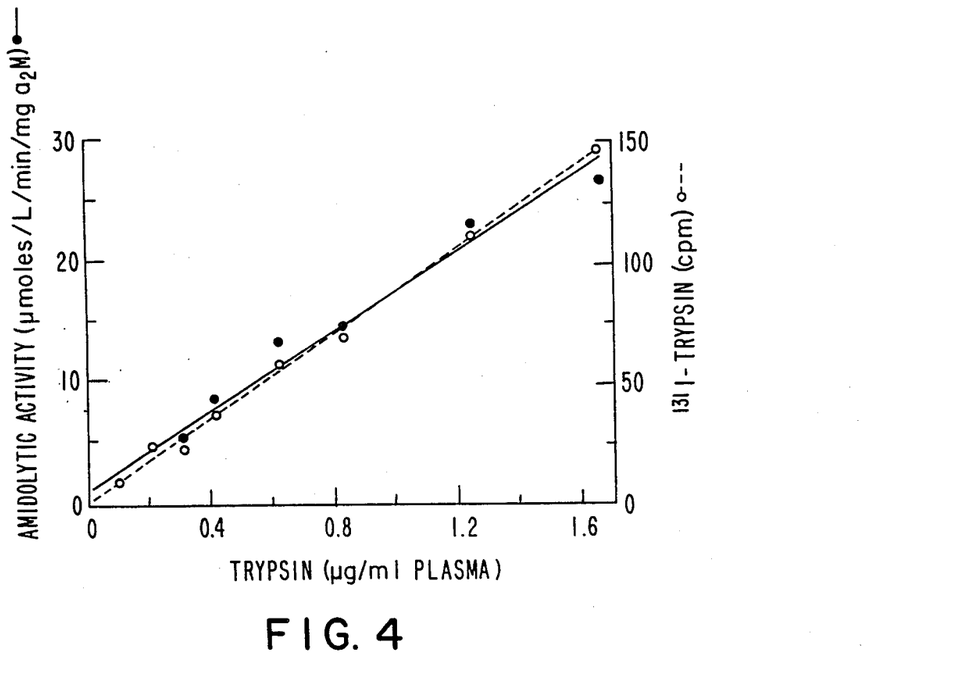

Studies on the binding of $\alpha_2$M-trypsin complexes in plasma by solid-phase $\alpha_2$M antibody. The demonstration that $\alpha_2$M in plasma could be quantitatively removed by immobilized $\alpha_2$M antibody made it possible to study the binding of exogenous $^{131}$I-$\beta$-trypsin to $\alpha_2$M in a plasma system. $^{131}$I-$\beta$-trypsin was added to plasma that contained 1.5 mg/ml $\alpha_2$M to give trypsin concentrations of 0.10 to 1.65 $\mu$g/ml plasma. This represents a trypsin/$\alpha_2$M molar ratio of 0.002 to 0.035. The plasma also contained a trace amount of $^{125}$I-$\alpha_2$M. Portions of plasma were indicated with solid-phase $\alpha_2$M antibody for two hours. The pellets were washed, counted for both $^{125}$I and $^{131}$I radioactivity and the amidolytic activity measured (FIG. 4). Whereas 86.7% of the $^{125}$I-$\alpha_2$M in the incubation mixture was bound to the antibody containing gel, only 50.3% of $^{131}$I-$\beta$-trypsin was similarly bound suggesting that trypsin also binds to other plasma proteins. The percent binding of both $\alpha_2$M and trypsin was unaffected by the varying concentrations of trypsin added to the plasma. The $^{131}$I radioactivity bound to the solid-phase antibody was proportional to the amount of $^{131}$I-trypsin in the original mixture.

To control for endogenous amidolytic activity, the solid-phase $\alpha_2$M antibody was incubated with a plasma-$^{125}$I-$\alpha_2$M mixture to which no $^{131}$I-trypsin had been added. The resulting $\alpha_2$M antibody gel hydrolyzed 2.4 $\mu$moles substrate/L/min/mg $\alpha_2$M corresponding to the addition to plasma of approximately 142 ng $\beta$-trypsin/ml. This background activity was substracted from the amidolytic activity of the gels incubated with the plasma, trypsin mixtures. The amidolytic activity of the $\alpha_2$M antibody gels incubated with the $^{131}$I-trypsin, plasma mixtures was proportional to the initial concentration of trypsin added, and parallel to the $^{131}$I counts bound to the gel (FIG. 4).

Figure 5:
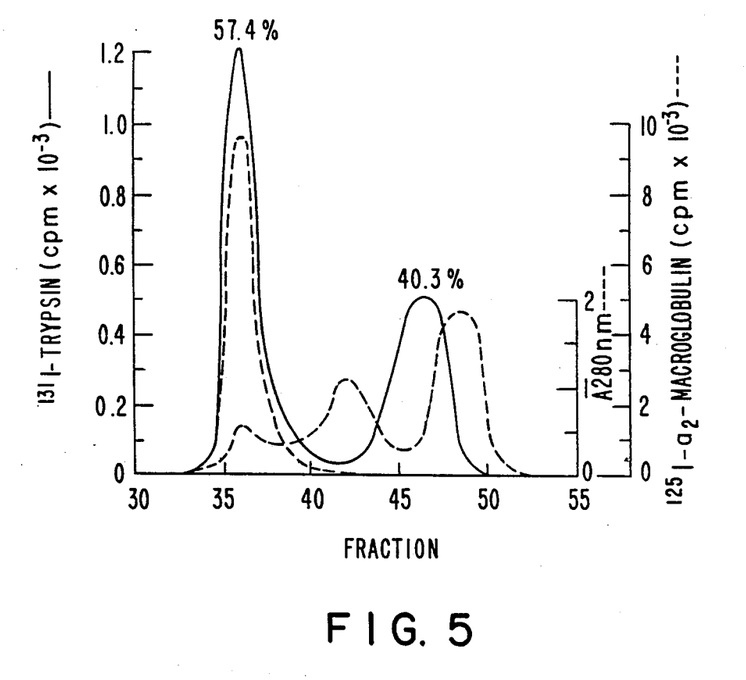
FIG. 5 is a graphic representation of gel filtration chromatography of a mixture of $^{131}$I-β-trypsin $^{125}$I-$\alpha_2$M, and plasma. To 1.0 ml plasma, $^{125}$I-$\alpha_2$M (36 μg) and $^{131}$I-β-trypsin (13 μg) were added and incubated 5 min at room temperature. The mixture was applied to a 1.4×70 cm column of Sephacryl S-200 gel filtration material (Pharmacia) maintained at 4° C. in 0.05M Tris-HCl, pH 8.0, containing 0.16M Citrate and 0.1M NaCl. 1.6 ml fractions were collected, counted for $^{125}$I and $^{131}$I in a γ counter, and the absorbance at 280 nm measured.

Analysis of a $^{131}$I-$\beta$-trypsin, plasma mixture by molecular sieve chromatography. From a comparison of the binding of $\alpha_2$M to the solid-phase $\alpha_2$M antibody in the experiment illustrated in FIG. 4 (86.7%), and the binding of $^{131}$I-trypsin (50.3%), it can be calculated that the total $\alpha_2$M in plasma should have bound 58.0% of the trypsin added to the plasma. Thus it seemed likely that approximately 42% of the trypsin may have been complexed to other plasma proteins and therefore unavailable to the $\alpha_2$M. To verify this possibility, a mixture of $^{131}$I-trypsin, $^{125}$I-$\alpha_2$M and plasma was fractionated by molecular sieve chromatography (FIG. 5). The major $^{131}$I-trypsin peak, containing 57.4% of the total $^{131}$I counts, co-eluted with the $^{125}$I-$\alpha_2$M in the first, high molecular weight protein peak. The second $^{131}$I-trypsin peak contained 40.3% of the total $^{131}$I counts and eluted earlier than the albumin peak at a position consistent with complex formation between trypsin and a plasma protein.

To further confirm the specificity of the insoluble $\alpha_2$M antibody, $\alpha_2$M-trypsin interaction and to identify the nature of the $^{131}$I-trypsin peaks from the gel filtration column, 0.6 ml of each peak fraction of $^{131}$I-trypsin was incubated with the solid phase $\alpha_2$M antibody (0.1 ml packed gel). Following an 18 h incubation, 99% of the $^{131}$I- M and 94% of the $^{131}$I-trypsin of the $\alpha_2$M peak fraction 36 was bound to the immobilized antibody. Less than 5% of $^{131}$I-trypsin was bound to the antibody gel in the incubation mixture of the second $^{131}$I-trypsin peak (fraction 46). Therefore most of the $^{131}$I-trypsin in the first high molecular weight peak was complexed with $\alpha_2$M. The failure of $^{131}$I-trypsin in the second radioactive peak to bind to the $\alpha_2$M antibody gel provides further evidence that trypsin had reacted with a protein other than $\alpha_2$M.

The process of the invention make possible the study of enzymes and inhibitor-enzyme complexes present in biological fluid, broadly and specifically presents a new approach to the study of the physiologic function of human plasma $\alpha_2$-macroglobulin. The method of the invention makes it possible to further characterize inhibitor-enzyme complexes and particularly the protease binding capacity of $\alpha_2$M in both purified systems and in complex biological fluids. As exemplified the solid-phase antibody-bound $\alpha_2$M- -trypsin complexes retain their ability to hydrolyze the tripeptide chromogenic substrate BzPhe-Val-Arg-NHNp with Michaelis-Menton constants identical to those of the soluble complexes. This indicates that the binding of the $\alpha_2$M-trypsin complex to an immobilized antibody does not appreciably effect the amidolytic activity of the bound protease. The antibody-bound $\alpha_2$M-trypsin complexes proved to be remarkably stable since they remain associated with the agarose gel matrix through repeated washings and assays of amidolytic activity. The finding that trypsin remains bound to $\alpha_2$M in the presence of substrate provides further evidence that trypsin binds to $\alpha_2$M at a site different from its catalytic site.

Studies of the conditions required to optimize substrate hydrolysis as in the Examiner showed that the optimum pH of the reaction for both the soluble $\alpha_2$M-trypsin complex as well as the solid-phase, antibody-bound complex was between 8 and 9. In contrast, Rindernecht, et al., *Biochem. Biophys. Acta*, 377: 158–165 (1975), using a different chromogenic substrate, N-carbobenzoxy-glycly-blycyl-L-arginine-2-naphthylamide HCl, found that catalysis was greatest at pH 10.0. They postulated that this degree of alkalinity was necessary to alter the microenvironment of the trypsin active site within the $\alpha_2$M-trypsin complex to that of free trypsin. It is not clear whether the difference in pH optimum between their study and ours reflects the behaviour of the purified $\beta$-trypsin used in the present study, the difference in substrate, or other factors.

We have demonstrated that the binding of $\alpha_2$M-trypsin complexes by immobilized $\alpha_2$M antibody also occurs when the assay system is applied to human plasma. Prior studies by Haverback et al., *J. Clin. Invest.*, 41:972–980 (1962) demonstrated that when trypsin was added to serum a complex was formed between trypsin and a serum protein that possessed an $\alpha_2$ ectrophoretic mobility Mehl et al., *Science*, 145:821–822 (1964) provided direct evidence that $\alpha_2$M was the protein responsible for this enzyme binding activity. In the present study, when plasma containing a trace quantity of $^{125}$I-$\alpha_2$M was incubated with immobilized $\alpha_2$M antibody, both radiolabeled and native $\alpha_2$M were bound. The electroimmunoassay technique of Laurell was used to establish that the binding of $^{125}$I-$\alpha_2$M to the solid-phase $\alpha_2$M antibody was proportional to the amount of unlabeled native $\alpha_2$M bound. The addition of the radiolabeled antigen to plasma made it possible, therefore, to quantitate the binding of plasma $\alpha_2$M to the solic-phase antibody. The binding of plasma $\alpha_2$M to the insoluble gel containing the antibody was specific since other immobilized antibodies such as anti-albumin, antihaptoglobin, or the IgG fraction of normal rabbit serum did not bind significant amounts of plasma $\alpha_2$M.

To establish that the solid-phase antibody technique detailed in this study could detect $\alpha_2$M-enzyme complexes in a biological fluid such as plasma, varying concentrations of $^{131}$I-$\beta$-trypsin were added to plasma that contained a trace quantity of $^{125}$I-$\alpha_2$M. Subsequent assay demonstrated that $\beta$-trypsin was found to the immobilized $\alpha_2$M antibody and that the amount of $^{131}$I-trypsin bound and the amidolytic activity associated with the solid-phase antibody was linearly related to the concentration of trypsin originally added to the plasma. Since control studies established that $^{131}I$-$\beta$-trypsin itself did not bind to the antibody gel, the trypsin activity that we observed was a specific measure of $\alpha_2$-trypsin complexes. At each concentration of trypsin added to plasma, 58% was bound to $\alpha_2M$, a finding explained by gel filtration studies that demonstrated that the remainder of the trypsin was associated with another protein, possibly $\alpha_1$-antitrypsin. These results parallel the findings of Ganrot, *Arkiv For Kemi Bd*, 26 Nr 50:577-582 (1967), who demonstrated that the affinity of trypsin for $\alpha_2M$ was greater than that for other trypsin inhibitors in plasma.

$\alpha_2M$ is a unique plasma protease inhibitor in that it forms a complex with an exceptionally wide variety of proteases including serine, thiol, carboxyl and metalloproteases derived from plasma, cells, or from microorganism; [Harpel et al. (1976), supra, Starkey et al., supra]. Complexes between $\alpha_2M$ and several different proteases have been identified in plasma; [Harpel et al., *J. Clin. Invest.*, 52: 2175-2184 (1973); Nilehn et al., *Scand. J. Clin. Lab. Invest.*, 20:113-121 (1967)], in peritoneal, [Ohlsson, *Bayer Symp. v. Proteinase Inhibitors*, Fritz et al., eds., Springer-Verlag, Berlin (1974) pp. 96-105], pleural [Bieth et al., *Clin. Chim. Acta*, 22:639-642 (1968); Bieth et al., *Clin. Chim. Acta*, 30:621-626 (1970)], and in synovial effusions [Shtacher et al., *Biochim. Biophys. Acta*, 303:138-147 (1973); Abe et al., *J Biochem.* (Tokyo), 71:919-922 (1973); Abe et al., *J. Biochem.* (Tokyo), 73:897-900 (1973)],however a convenient method suitable for the quantitative analysis of these complexes has not previously been available. The solid-phase $\alpha_2M$ antibody technique described in this study facilitates the rapid isolation and concentration of enzyme-enzyme inhibitor complexes generally of $\alpha_2M$-protease complexes specifically and the measurement of their presence and/or catalytic capacity in biological fluids in various physiologic and pathologic states. Modifications of the assay conditions will permit the measurement of the activity of physiologically important enzymes and enzyme inhibitors, particularly proteases such as thrombin, plasmin and plasma kallikrein when bound to $\alpha_2M$.

EXAMPLE II

This example demonstrates an enzyme-linked differential antibody immunosorbent assay for the quantitation of $\alpha_2$-plasmin inhibitor-plasmin and $\alpha_2$-macroglobulin-plasmin complexes. In this example, the inhibitor-plasmin complex is bound to a surface by an inhibitor specific antibody, then the plasmin bound to the inhibitor is quantified by a second antibody, rabbit antiplasminogen F(ab')$_2$, labeled with alkaline phosphatase. The hydrolysis of p-nitrophenyl phosphate by the alkaline phosphatase is expressed in fmol plasminogen/ml utilizing a standard plasminogen curve. Inhibitor-enzyme complexes were generated in plasma by the addition of plasmin or of urokinase (UK). The concentration of plasmin added was well below the plasma concentration of $\alpha_2$-plasmin inhibitor (1 $\mu M$) or of $\alpha_2$-macroglobulin (3.5 $\mu M$), so that neither inhibitor would be fully saturated with enzyme. Under these conditions, increasing amounts of plasmin generated an increase in both $\alpha_2$-plasmin inhibitor-plasmin and $\alpha_2$-macroglobulin-plasmin complexes. Varying amounts of plasmin were incubated with each of the purified inhibitors in the concentration found in plasma and the complexes that formed were quantitated by immunoassay. These studies made it possible to quantitate the distribution of plasmin between the two inhibitors in plasmin or UK-treated plasma. In plasmin-treated plasma, 10 percent or less of the plasmin bound to both inhibitors was in complex with $\alpha_2$-macroglobulin. In contrast, between 19-51 percent of the plasmin generated in UK-activated plasma was bound to $\alpha_2$-macroglobulin. Thus major changes in the distribution of plasmin were observed depending upon whether plasmin was added to plasma or whether plasminogen was activated endogenously. Twenty-three normal individuals had low levels of $\alpha_2$-plasmin inhibitor-plasmin complexes (4.1±3.5 fmol/ml) whereas six patients with laboratory evidence for disseminated intravascular coagulation demonstrated a sixteen to thirty-five-fold increase in the concentration of these complexes. These da&a indicate that a useful new probe for the study of the fibrinolytic enzyme system has been developed.

This study details a novel method for detection and quantitation of $\alpha_2$-plasmin inhibitor-plasmin and $\alpha_2$-macroblobulin-plasmin complexes. The method is based on the immunocapture of the inhibitor-enzyme complex by an antiinhibitor antibody adsorbed to the surface of a plastic microtitration plate. After eliminating the unbound protein by washing, alkaline phosphatase labeled immunospecific antiplasminogen F(ab')$_2$ fragments are added to detect the plasmin in complex with its inhibitor. This methodology has made it possible to follow the generation of $\alpha_2$-plasmin inhibitor-plasmin and $\alpha_2$-macroglobulin-plasmin complexes in plasma to which plasmin is added. The $\alpha_2$-plasmin inhibitor-plasmin complex was detected when as little as 6.7 nM plasmin was added. Since the approximate plasminogen concentration in plasma is 2.5 $\mu M$, the amount of plasmin added is equivalent to a 0.3% conversion of plasma plasminogen to plasmin. $\alpha_2$-Macroglobulin-plasmin complexes were detected when 160 nM plasmin were added to plasma. Since plasma contains about 1 $\mu M$ of $\alpha_2$-plasmin inhibitor, it is apparent that $\alpha_2$-macroglobulin binds plasmin in plasma well below the saturation level of $\alpha_2$-plasmin inhibitor. These data indicate that recent conclusions that plasmin forms a complex with $\alpha_2$-macroglobulin only following saturation of $\alpha_2$-plasmin inhibitor must be revised; Mullertz et al, *Biochem. J.* (London), 159:545-553 (1976); Collen, *Eur. J. Biochem.*,69:209-216 (1976).

The ability of the new assay described in this study to measure both $\alpha_2$-plasmin inhibitor-plasmin and $\alpha_2$-macroglobulin-plasmin complexes in plasma has produced an unanticipated result. There appears to be a major difference in the distribution of plasmin between $\alpha_2$-plasmin inhibitor or $\alpha_2$-macroglobulin depending upon whether preformed plasmin is added to the plasma or the plasminogen in plasma is activated endogenously with urokinase. When plasmin is added to plasma at concentrations well below the molar binding activity of $\alpha_2$-plasmin inhibitor, over 90 percent of the plasmin associated with the two inhibitors is complexed with $\alpha_2$-plasmin inhibitor. In urokinase-activated plasma, however, when the $\alpha_2$-plasmin inhibitor-plasmin complex activity is equivalent to that in plasmin-treated plasma and where $\alpha_2$-macroglobulin-plasmin complexes are still undetectable, over 40% of the plasmin bound to both inhibitors is complexed with $\alpha_2$-macroglobulin.

Although our data do not explain why plasmin is distributed differently between the two inhibitors depending upon whether plasmin is activated endogenously or added to the plasma, recent observations by Lijnen, et al, *J. Biol. Chem.*, 255:10214-10222 (1980), may provide an explanation. These authors demonstrated that the plasma protein histidinerich glycoprotein, first isolated by Haupt and Heimburger, Haupt et al, *Hoppe-Seyler's Z. Physio. Chem.*, 353:1125-1132 (1972) and Heimburger et al, *Hope-Seyler's Z. Physiol. Chem.*, 353:1133-1140 (1972) interacts with the high affinity lysine-binding site in plasmin to markedly reduce the reaction rate between plasmin and $\alpha_2$-antiplasmin. They postulated that about one half of the plasminogen in blood is complexed reversibly with the histidine-rich glycoprotein. Thus, a plausible explanation for the results in the present study is that when preformed plasmin, free of histidine-rich glycoprotein, is added to plasma, it rapidly binds to $\alpha_2$-plasmin inhibitor. However, a portion of the plasminogen in plasma, when activated by urokinase, is complexed with the histidinerich glycoprotein and thereby loses its $\alpha_2$-plasmin inhibitor high affinity binding site. Presumably a portion of this form of plasmin binds to $\alpha_2$-macroglobulin. Studies to confirm the possibility that the histidine-rich protein may modulate the distribution of plasmin between its circulating inhibitors have been initiated.

In order to explore the potential usefulness of this new assay, the plasma of patients with laboratory evidence of overt disseminated coagulation were studied. The immunoassay demonstrated a sixteen to thirty-five fold increase in levels of $\alpha_2$-plasmin inhibitor-plasmin complexes in the patient group indicating that this assay can detect plasmin formation in vivo. Study of $\alpha_2$-macroglobulin-plasmin complexes in patients' plasma demonstrated minimal elevations. These results are compatible with the lower sensitivity of the immunoassay for $\alpha_2$-macroglobulin-plasmin complexes as compared to the $\alpha_2$-plasmin inhibitor-plasmin complexes. Differential clearance rates of the two-plasmin complexes may also explain our findings. In the experimental animal, $\alpha_2$-macroglobulin-enzyme complexes are cleared in less than 60 minutes, Blatrix et al, *Path. Biol.*, 21:11-14 (1973), faster than the T ½ of 0.5 days reported for the $\alpha_2$-plasmin inhibitor-plasmin complex, Collen et al, *Blood*, 53:313-324 (1979).

Our results indicate that the enzyme-linked differential antibody assay as detailed in this report serves as sensitive probe for quantitating activation of the fibrinolytic enzyme system in purified systems, in plasma in vitro, and in the circulation. Using this assay, it has been found that the distribution of plasmin between $\alpha_2$-plasmin or $\alpha_2$- macroglobulin differs according to whether plasmin is added to the plasma or endogenous plasma plasminogen is activated with urokinase. The immunocapture assay has established that circulating inhibitor-plasmin complexes are elevated in patients with disseminated introvascular coagulation. Thus, a new approach for the study of the fibrinolytic enzyme system has been developed. The methods described may also prove valuable in the detection and quantitation of other biologically important protein complexes.

Blood samples. Venous blood was obtained from normal volunteers in plastic syringes and added to 3.8% sodium citrate (9/1, v/v). Alternatively, portions of blood samples sent to the Blood Coagulation Laboratory of the New York Hospital for coagulation studies were tested for plasmin inhibitor-plasmin complexes. The plasma, harvested following centrifugation at 2500 rpm for 20 min, was frozen in plastic tubes at $-70°$ C.

Purification of human plasma proteins. $\alpha_2$-Plasmin inhibitor was isolated from outdated blood bank plasma as described by Moroi et al, *J. Biol. Chem.*, 251:5956-5965 (1976). The final preparation contained no detectable $\alpha_2$-macroglobulin, C1 inactivator, $\alpha_2$-antitrypsin, antithrombin III, inter-$\alpha$-trypsin inhibitor or chymotrypsin inhibitor as analyzed by double diffusion in agarose gels using specific antibodies obtained from Behring Diagnostics, American Hoechst Corp., Somerville, N.J. A reference standard of $\alpha_2$-plasmin inhibitor was also kindly provided by Dr. Désiré Collen. $\alpha_2$-Macroglobulin was isolated from fresh human plasma as has been previously described; Harpel, "Methods in Enzymology, Proteolytic Enzymes," Lorand, Academic Press, Inc., New York; 45:639-652 (1976); Harpel et al, *J. Biol. Chem.*, 254:8669-8678 (1979). Plasminogen was isolated from plasma by lysine affinity chromatography; Deutsch et al, *Science*, 170:1095-1096 (1970), followed by gel filtration chromatography (Bio-Gel A-0.5 m, Bio-Rad Laboratoreis, Richmond, CA). The concentration of each protein was determined by their extinction coefficient [$\alpha_2$-plasmin inhibitor=7.03, Moroi et al, *J. Biol. Chem.*, 251:5956-5965 (1976); $\alpha_2$-macroglobulin=8.93, Hall et al, *Biochem. J. (London)*, 171:27-38 (1978); plasminogen=17.0, Robbins et al, "Methods in Enzymology: Proteolytic Enzymes", Perlmann et al, Academic Press, New York 19:184-199 (1970)].

Plasminogen was activated with insolubilized urokinase in 0.1 M barbital buffer, pH 8.3, containing 25 percent glycerol. The urokinase (Abbott Laboratories, North Chicago, IL) was coupled to Bio-Gel A 5.0 m (Bio-Rad Laboratoreis) by the cyanogen bromide method, March et al, *Anal. Biochem.*, 60:149-152 (1974). Each gram of activated gel was coupled with 125,000 units of urokinase. In a typical activation mixture, plasminogen (6.6 mg) was incubated with insolubilized urokinase (0.3 ml packed gel) in a total volume of 1.0 ml, at room temperature for 16 hours. The activity of the plasmin was established by active site titration; Chase, Jr. et al, *Methods in Enzymol*, 19:20-27 (1970). The plasmin was stored at $-70°$ C. in 50% glycerol, at a concentration of 2.0 mg/ml active plasmin.

Preparation of antisera and immunoglobulin fractions. Rabbits were immunized intradermally with $\alpha_2$-plasmin inhibitor, $\alpha_2$-macroglobulin or plasminogen in equal volumes of complete Freund's adjuvant. The IgG of the antisera was isolated, following dialysis against 0.02 M $K_2HPO_4$ buffer, pH 8.0, by chromatography on DE-52 cellulose (H. Reeve Angel & Co., Clifton, NJ) to which cibacron-blue F 3GA (Polyscience, Inc., Warrington, PA) was coupled, Travis et al, *Biochem. J.*, 157:301-306 (1976). The rabbit anti-$\alpha_2$-plasmin inhibitor or anti-$\alpha_2$-macroglobulin IgG fraction was absorbed with insolubilized human plasminogen to remove any plasminogen reactive antibody.

To minimize the occurrence of spurious high values in the immunoassay caused by naturally occurring human antibodies directed against the Fc portion of immunoglobulin molecules (Rheumatoid factor), Johnson et al, *Clin. Immunol. Immunopath.*, 6:414-430 (1976), F(ab')$_2$ fragments were prepared from the rabbit anti-plasminogen IgG and subsequently labeled with alkaline phosphatase. The F(ab')$_2$ fragments were prepared by digestion of rabbit anti-human plasminogen IgG with 0.2 mg of pepsin per 100 mg of IgG (pepsin, 2700 U/mg, Worthington Biochemical Corp., Freehold, NJ) in 0.1 M sodium acetate buffer, pH 4.0 for six hours at 37° C.; Nisonoff, *Methods Med. Res.*, 10:134-141 (1964). After adjusting the pH to 7.4 with 1 M Tris base, the digest was passed through two columns in series, the first containing 6.0 ml Protein A-Sepharose CL-4B (Pharmacia) to bind undigested IgG and pFc fragments, and the second containing immobilized human plasminogen (5 mg/ml Sepharose CL-4B, coupled by the method of March et al, supra. After washing the insoluble plasminogen antigen column with sodium phosphate buffer (0.1 M), pH 7.0, containing NaCl (0.25 M) and 0.5% Tween 80, the immunospecific F(ab')$_2$ fragments were eluted with 0.1 M glycine-HCl, pH 2.5, into tubes containing K$_2$CO$_3$(2 M). The yield of F(ab')$_2$ from 50.0 ml of rabbit antisera was 22 mg.

Enzyme-linked differential antibody immunosorbent assay. The strategy for detecting plasmin inhibitor-plasmin complexes by the immunoassay developed in this study is indicated in FIG. 6. The performance of the assay was essentially as detailed by Voller et al, "Manual of Clinical Immunology," Rose et al, American Society of Microbiology, Washington, D. C. 506–512 (1976). Microtitration plates (Linbro, E.I.A. Microtitration Plate, Flow Laboratories, Inc., Hamden, CT) were coated with the IgG fraction of normal rabbit serum, or of the antisera against $\alpha_2$-plasmin inhibitor or $\alpha_2$-macroglobulin. Thus, 0.2 ml portions of the IgG in the bicarbonate coating buffer were incubated in a humid chamber overnight at 4° C. Preliminary studies using IgG concentrations ranging from 1.25 to 20 μg/ml demonstrated that optimal binding of either $\alpha_2$-plasmin inhibitor-, or $\alpha_2$-macroglobulin-plasmin complexes in plasma to which either plasmin or urokinase had been added occurred at IgG concentration of 2.5 μg/ml or greater. A concentration of 6.0 μg IgG/ml in coating buffer, therefore, was employed in this study. Contents of the microtitration plates were removed, and the wells washed three times, for three min each in PBS-Tween (phosphate buffered saline, 0.15 M, pH 7.4, containing 0.05% Tween 20). The solutions containing the inhibitor-plasmin complexes were diluted in PBS-Tween buffer containing 0.05 M epsilon amino caproic acid (EACA) to prevent plasminogen activation subsequent to dilution. These mixtures (0.2 ml) were added in duplicate to coated wells and the plates incubated for two hours at 37° C., then for an additional two hours at 4° C. in a humid chamber. The washing procedure was repeated and the alkaline phosphatase labeled anti-plasminogen F(ab')$_2$, prepared as detailed below, was added for an 18 hour incubation in a humid chamber at 4° C. The wells were then emptied, the wash step repeated, and the substrate (0.2 ml) p-nitrophenyl phosphate (Sigma) (1 mg/ml in 10 percent diethanolamine buffer, pH 9.8) added. The color development was followed at 10 min intervals by repeated readings at 405 nm in a Titertek Multiscan photometer (Flow Laboratories, McLean, Va.) The change in absorbance per min was calculated by subtracting the 10 min value from the 60 min reading and dividing by 50. When the reading was greater than 2.0, a shorter time interval was employed. Plots of the color development with time demonstrated a linear relationship.

Alkaline phosphatase labeling of anti-human plasminogen F(ab')$_2$ was performed as described by Voller, et al, supra, using Sigma Type VII, calf mucosa alkaline phosphatase. The activity of the labeled antibody preparations was assessed by coating the microtitration plates with plasminogen (1 μg/ml in carbonate coating buffer) for 18 hours in a humid chamber, 4° C. After washing three times for three min each in PBS-Tween, dilutions of the stock alkaline phosphatase labeled immunoglobulin preparation (1/200–1/1600) were then added. Following an overnight incubation at 4° C., and washing, 0.2 ml of the substrate p-nitrophenyl phosphate was added, and the absorbance followed with time at 405 nm. The concentration producing the highest reading (1/400 dilution) was selected for the present studies.

Plasminogen standard curve. A standard curve was generated with each experiment. Purified human plasminogen, diluted from 1.25 to 25 ng/ml in carbonate coating buffer in glass tubes, was passively adsorbed in duplicate (0.2 ml portions) to the wells of microtitration plates, 18 hours at 4° C. in a humid chamber. The wells were washed three times with PBS-Tween, and the alkaline phosphatase labeled anti-plasminogen F(ab')$_2$ antibody added for an additional 18 h at 4° C. The washing step was repeated, the p-nitrophenyl phosphate substrate added, and the change in absorbance monitored. The best fit curve of the change in absorbance (405 nm), plotted against plasminogen concentration was calculated by linear regression analysis using a statistical package supplied by Hewlett Packard and a Hewlett Packard Model 9815A calculator with a Model 9862A X-Y Plotter. The concentration of plasminogen was converted to fmol/ml (plasminogen Mr=92,000). For the standard plasminogen curve illustrated (FIG. 7), the $\Delta A_{405}$ nm/min/fmol/ml is $1.81 \times 10^{-4}$.

Assay of purified $\alpha_2$-plasmin inhibitor-plasmin and $\alpha_2$-macroglobulin plasmin complexes. Plasmin, in concentrations ranging from 128 ng to 2.048 μg, diluted in glass tubes in barbital buffer containing 25% glycerol, or buffer alone were added to purified $\alpha_2$-plasmin inhibitor (6.0 μg) or to $\alpha_2$-macroglobulin (200 μg) in a total volume of 0.1 ml and incubated 10 min, 37° C. PBS-Tween buffer containing EACA (0.05 M) was added to a total volume of 4.0 ml. Each final inhibitor concentration was, therefore, equivalent to the concentration of a 1/40 dilution of normal plasma. Portions (0.2 ml) were added in duplicate to microtitration plate wells coated with rabbit anti-$\alpha_2$-plasmin inhibitor IgG, anti-$\alpha_2$-macroglobulin IgG or with normal rabbit IgG (5 μg/ml in carbonate buffer). Following an incubation period (2 hours, 37° C.; 2 hours, 4° C.) and a washing step, the antiplasminogen F(ab')$_2$ labeled with alkaline phsophatase was added. After 18 hours at 4° C. and repeat washing, p-nitrophenyl phosphate was added and the absorbance recorded. The change in absorbance per min obtained using normal rabbit IgG was subtracted from those values obtained using the specific antisera. Results were converted to plasminogen equivalents using a standard plasminogen curve.

Quantitation of circulating plasmin inhibitor-plasmin complexes by the enzyme-linked differential antibody immunosorbent assay. Various plasma samples from normal individuals or from hospitalized patients who were studied in the clinical coagulation laboratory were diluted 1/40 in PBS-Tween buffer containing 0.05 M EACA. Portions (0.2 ml) in duplicate were added to microtitration plate wells coated with normal rabbit IgG, or with anti-$\alpha_2$-plasmin inhibitor of anti-$\alpha_2$-macroglobulin IgG (5.0 μg/ml). After an incubation of 2 hr at 37° C., and 2 hr at 4° C. in a humid chamber, and a washing step, rabbit anti-plasminogen F(ab')$_2$ labeled with alkaline phosphatase (0.2 ml) was added and incubated 18 h at 4° C. Following a washing step the substrate, p-nitrophenyl phosphate, was added, and the absorbance recorded. The change in absorbance per minute of the plasma sample added to the well coated with nromal rabbit IgG was substrated from the value that resulted when the sample was added to the wells coated with antibody directed against either $\alpha_2$-plasmin inhibitor or $\alpha_2$-macroglobulin. This $\Delta A_{405\ nm}$ was then divided by the change in absorbance per min per fmol plasminogen, derived from a plasminogen curve run simultaneously, as detailed above. The final results were expressed in plasminogen equivalents, in fmol plasminogen per ml.

Fibrin degradation products were determined using a coated latex particle test kit (Thrombo-Wellcotest, Wellcome Research Laboratories, Beckenham, England) as described in the manufacturer's instructions.

Plasminogen standard curve. Plasminogen, in increasing concentrations, was passively adsorbed to the wells of the plastic microtitration plate and rabbit anti-plasminogen F(ab')$_2$ labeled with alkaline phosphatase was added. The resulting hydrolysis of the alkline phosphatase substrate p-nitrophenyl phosphate was linear with the amount of plasminogen added in the concentration range of 1.25 to 25 ng/ml (FIG. 7). Thus, hydrolysis of substrate was proportional to plasminogen concentration. This plasminogen curve was repeated with each experiment detailed in this report, and hydrolysis of substrate is expressed by conversion from the standard curve to plasminogen equivalents in fmol/ml.

Detection and quantitation of $\alpha_2$-plasmin inhibitor, $\alpha_2$-macroglobulin-plasmin complexes in plasma. Increasing concentrations of plasmin, activated by insoluble urokinase, were added to plasma in order to generate plasmin inhibitor-plasmin complexes. As illustrated in FIG. 8, $\alpha_2$-plasmin inhibitor-plasmin complexes were first identified at added plasmin concentrations of 6.7 nM (0.5 µg/ml plasma), and $\alpha_2$-macroglobulin-plasmin complexes at 160 nM (12.0 µg/ml). The concentration of both complexes increased with increasing concentration of exogenously added plasmin; however, much less activity appeared to be associated with the $\alpha_2$-macroglobulin-plasmin complexes than with the $\alpha_2$-plasmin inhibitor-plasmin complexes.

Inhibitor-plasmin complexes were also detected in plasma to which increasing concentrations of urokinase, the plasminogen activator, were added (FIG. 9). Both $\alpha_2$-plasmin inhibitor-plasmin and $\alpha_2$-macroglobulin-plasmin complexes were detected at 31.25 units urokinase per ml plasma following a 30 min incubation. As with the addition of plasmin, increasing concentrations of urokinase produced increasing amounts of both complexes. In striking contrast, however, to the complexes generated with plasmin, there appeared to be proportionally more $\alpha_2$-macroglobulin-plasmin complexes formed in relationship to the $\alpha_2$-plasmin inhibitor-plasmin complexes in urokinase-activated plasma.

Quantitation of purified $\alpha_2$-plasmin inhibitor or $\alpha_2$-macroglobulin-plasmin complexes. To further define the distribution of plasmin between $\alpha_2$-plasmin inhibitor and $\alpha_2$-macroglobulin, the immunoreactivity of plasmin bound to each purified inhibitor was examined (FIG. 10). The concentration of each inhibitor used was similar to that found for the normal plasma that was diluted 1/40 for the assay. Thus, plasmin was added to $\alpha_2$-plasmin inhibitor (1.5 µg/ml) or $\alpha_2$-macroglobulin (50 µg/ml) so that the molar ratios of the enzyme to $\alpha_2$-plasmin inhibitor was 0.018 to 0.29 and to $\alpha_2$-macroglobulin was 0.006 to 0.096. Each of the purified complexes were added to microtitration plate wells coated with the inhibitor antibody. The IgG fraction of rabbit $\alpha_2$-plasmin inhibitor antisera did not bind $\alpha_2$-macroglobulin-plasmin complexes as compared to the control rabbit IgG nor did the rabbit $\alpha_2$-macroglobulin antisera bind $\alpha_2$-plasmin inhibitor-plasmin complexes. These experiments demonstrate the lack of cross-reactivity in the enzyme-linked assay, and further confirm its specificity.

Increasing concentrations of plasmin added to each inhibitor yielded a linear increase in reactivity with the enzyme-linked plasminogen antibody when the inhibitor-enzyme complex was bound to the microtitration plate wells by the specific anti-inhibitor antibody (FIG. 10). The sensitivity of the assay is greater for the $\alpha_2$-plasmin inhibitor-plasmin complex than for the $\alpha_2$-macroglobulin-plasmin complex. The ratio of the slopes of the two curves in FIG. 10 is 3.6. These standard curves permit direct comparison of the binding of plasmin to each inhibitor when either plasmin or urokinase is added to plasma. The activity of the $\alpha_2$-plasmin inhibitor-plasmin or $\alpha_2$-macroglobulin-plasmin complexes at each concentration of plasmin (FIG. 8) or urokinase (FIG. 9) added to plasma, was converted to nM plasmin bound to each inhibitor by referring to the purified inhibitor curves (FIG. 10). The percent plasmin bound to $\alpha_2$-macroglobulin compared to the total bound to both inhibitors in treated plasma was then plotted against the activity of the $\alpha_2$-plasmin complex in each plasma sample expressed in plasminogen equivalents (FIG. 11).

In urokinase-activated plasma, the $\alpha_2$-macroglobulin-plasmin complex increased from 19 to 51 percent as the concentration of activator increased from 75 to 500 units per ml plasma. Thus, for example, when 125 units of urokinase are added per milliliter plasma, the activity of the $\alpha_2$-plasmin inhibitor-plasmin and the $\alpha_2$-macroglobulin-plasmin complexes are 38.5 and 8.83 fmol plasminogen equivalents/ml respectively (FIG. 9). This amount of activity in the purified system is equivalent to the addition of 64.4 nM plasmin to $\alpha_2$-plasmin inhibitor and 43.0 nM plasmin to $\alpha_2$-macroglobulin (FIG. 10). The ratio of plasmin bound to $\alpha_2$-macroglobulin compared to the total bound when 125 units of urokinase are added to plasma is, therefore, 43.0/107.4, or 40% (FIG. 11). Since the concentration of $\alpha_2$-plasmin inhibitor in plasma is 1.0 µM and of $\alpha_2$-macroglobulin, 3.5 µM, it is apparent that in urokinase-activated plasma, the plasmin that is generated binds to both inhibitors before stoichiometric saturation of $\alpha_2$-plasmin inhibitor occurs.

In contrast to the findings in urokinase-activated plasma, much less plasmin binds to $\alpha_2$-macroglobulin, and proportionally more to $\alpha_2$-plasmin inhibitor when the active enzyme plasmin is added to plasma (FIG. 11). With increasing concentrations of plasmin, the percent bound to $\alpha_2$-macroglobulin increases progressively to 10.5%, at an added plasmin concentration of 150 nM. It is also apparent that in urokinase-activated plasma, $\alpha_2$-macroglobulin-plasmin complexes become detectable at lower levels of $\alpha_2$-plasmin inhibitor-plasmin complex activity. $\alpha_2$-Macroglobulin-plasmin complexes are detected in urokinase-activated plasma when the activity of the $\alpha_2$-plasmin inhibitor-plasmin complex is approximately 24 fmol plasminogen equivalents/ml. In plasmin-treated plasma, however, the $\alpha_2$-macroglobulin-plasmin complex is not detected until an $\alpha_2$-plasmin inhibitor-plasmin complex activity of 75 fmol plasminogen equivalents/ml is reached. These results demonstrate that the distribution of plasmin between the two inhibitors studied differs markedly depending on whether plasmin is activated endogenously in plasma or is added directly to plasma.

Measurement of $\alpha_2$-plasmin inhibitor-plasmin or $\alpha_2$-macroglobulin-plasmin complexes in the plasma of patients with disseminated intravascular coagulation. The enzyme-linked differential antibody immunosorbent assay was used to quantitate $\alpha_2$-plasmin inhibitor-plasmin or $\alpha_2$-macroglobulin-plasmin complexes in the plasma of healthy individuals, or in the plasma of six patients with laboratory evidence for disseminated intravascular coagulation (Table 2).

TABLE 2

$\alpha_2$-Plasmin Inhibitor-Plasmin Complexes in the Blood of Patients with Disseminated Intravascular Coagulation

| Patient | Diagnosis | Fibrinogen mg/dl | Thrombin Clotting Time s | Fibrinogen Degradation Products µg/ml | Platelets ml$^{-1}$ | $\alpha_2$-Plasmin Inhibitor-Plasmin Complexes fmol/ml |
|---|---|---|---|---|---|---|
|  | Normal range | 180–400 | 18–21 | <10 | 180,000–400,000 | 4.1 ± 3.5 (N = 23) |
| 1. | Adenocarcinoma liver | 75 | 36 | >40 | 101,000 | 79.3 |
| 2 | Hemorrhagic shock | 148 | — | >40 | 79,000 | 141.8 |
| 3. | Acute promyelocytic leukemia | 119 | 33 | >10 < 40 | 75,000 | 141.1 |
| 4. | Epidermoid carcinoma of lung | 130 | 48 | >10 < 40 | Decreased on peripheral smear | 65.9 |
| 5. | Sepsis; Hepatic failure | 65 | 48 | >10 < 40 | 48,000 | 67.2 |
| 6. | Sepsis | 105 | >120 | >40 | 49,000 | 93.5 |

The mean and S.D. of $\alpha_2$-plasmin inhibitor-plasmin complex levels of 23 normal individuals were 4.1±3.5 with a range of 0–11.1 fmol/ml. The patients studied had depressed fibrinogen levels an platelet counts, prolonged thrombin times and elevated fibrin degradation products. $\alpha_2$-plasmin inhibitor-plasmin complex levels in this group with overt defibrination varied between 65 and 142 fmol/ml. In contrast to the results with $\alpha_2$-plasmin ingibitor-plasmin complexes, quantitation of $\alpha_2$-macrogrobulin-plasmin complexes failed to detect significant differences in the patients as compared to the control group. (Abbreviations used in this Example:

PBS-Tween, phosphate buffered saline contained Tween;
EACA, epsilon amino caprioc acid;
FDP, fibrin degradation products;
PI, $\alpha_2$-plasmin inhibitor;
$\alpha_2$M, $\alpha_2$-macroglobulin;
UK, urokinase

What is claimed is:

1. A method of analyzing biological fluid for naturally occurring proteolytic enzyme inhibitor-proteolytic enzyme complexes which comprises:
    (a) forming an insoluble immobilized immunocaptured naturally occurring proteolytic enzyme inhibitor-proteolytic enzyme complex comprising proteolytic enzyme, naturally occurring proteolytic enzyme inhibitor present in said biological fluid, and enzyme inhibitor antibody or an inhibitor reactive fragment thereof, and
    (b) detecting the enzyme or enzyme inhibitor-enzyme complex in the insoluble immobilized immunocaptured complex.

2. The method of claim 1 wherein immobilized naturally occurring proteolytic enzyme inhibitor-proteolytic enzyme complex is affixed to a solid or semisolid matrix by means of the inhibitor antibody or active fragment thereof.

3. The method of claim 1 or 2 wherein the enzyme inhibitor is $\alpha_2$-macroglobulin.

4. The method of claim 1 or 2 wherein the enzyme inhibitor is $\alpha_2$-macroglobulin and the matrix is an agarose gel.

5. The methods of claims 1 or 2 wherein the biological fluid is a human biological fluid.

6. A method which comprises:
    (a) affixing an enzyme inhibitor antibody against a naturally occurring proteolytic enzyme inhibitor or inhibitor reactive fragment thereof to a solid or semi-solid matrix
    (b) contacting the resultant insoluble inhibitor reactive matrix with a biological fluid to capture naturally occurring enzyme inhibitor-enzyme complex from said fluid
    (c) analytically determining the identity or quantity of the captured enzyme.

7. The method as in claim 6 wherein the captured naturally occurring proteolytic enzyme inhibitor-proteolytic enzyme complex is enzymatically reactive and the analytical determination comprises reacting the insoluble immobilized complex against substrates reactive to the captured enzyme.

8. The method as in claim 6 wherein the enzyme inhibitor is $\alpha_2$-macroglobulin.

9. The method as in claim 6 wherein the insoluble captured naturally occurring proteolytic enzyme inhibitor-proteolytic enzyme complex is not enzymatically reactive and the analytical determination comprises reacting the immobilized complex with a detection facilitating material which reacts with a site specific to the bound enyzme or the enzyme inhibitor-enzyme complex.

10. A method of analyzing biological fluid for naturally occurring proteolytic enzyme inhibitor-proteolytic enzyme complexes which comprises:
    (a) forming an insoluble immobilized immunocaptured reaction product of a naturally occurring proteolytic enzyme inhibitor-proteolytic enzyme complex present in said biological fluid and an antibody against said naturally occurring inhibitor or a reactive fragment of said antibody and
    (b) detecting the enzyme or enzyme inhibitor-enzyme complex in the immobilized immunocaptured complex.

11. The method of claim 10 wherein the proteolytic enzyme is selected from the group consisting of plasmin, thrombin, kallikrein, Cl, factor $X_a$, Hageman factor, trypsin, leukocyte elastase, pancreatic elastase, chymotrypsin, collagenase, cathespin G and cathespin B.

12. The method as in claims 10 or 11 wherein the maturally occurring proteolytic enzyme inhibitor is selected from the group consisting of alpha 2-plasmin inhibitor, alpha 2-macroglobulin, alpha 1-anti-trypsin, Cl inhibitor and antithrombin-heparin cofactor.

13. The method of claim 10 wherein the naturally occurring proteolytic enzyme inhibitor is $\alpha_2$ plasmin inhibitor, wherein the proteolytic enzyme is plasmin, and wherein the bound $\alpha_2$ plasmin inhibitor-plasmin complex is measured by measuring complexed plasmin.

* * * * *